US007772227B2

(12) United States Patent
Adam-Worrall

(10) Patent No.: US 7,772,227 B2
(45) Date of Patent: Aug. 10, 2010

(54) TRICYCLIC 1-[(INDOL-3-YL)CARBONYL]PIPERAZINE DERIVATIVES AS CANNABINOID CB1 RECEPTOR AGONISTS

(75) Inventor: Julia Adam-Worrall, New House (GB)

(73) Assignee: N.V. Organon, Oss (NL)

( * ) Notice: Subject to any disclaimer, the term of this patent is extended or adjusted under 35 U.S.C. 154(b) by 112 days.

(21) Appl. No.: 10/583,013

(22) PCT Filed: Dec. 13, 2004

(86) PCT No.: PCT/EP2004/053421

§ 371 (c)(1),
(2), (4) Date: Jun. 15, 2006

(87) PCT Pub. No.: WO2005/058327

PCT Pub. Date: Jun. 30, 2005

(65) Prior Publication Data

US 2007/0088025 A1    Apr. 19, 2007

Related U.S. Application Data

(60) Provisional application No. 60/530,528, filed on Dec. 17, 2003.

(51) Int. Cl.
*A61K 31/5365* (2006.01)
*A61K 31/496* (2006.01)
*A61K 31/4985* (2006.01)

(52) U.S. Cl. ............ 514/224.5; 514/230.2; 514/253.03; 544/32; 544/101; 544/361

(58) Field of Classification Search ............... None
See application file for complete search history.

(56) References Cited

U.S. PATENT DOCUMENTS

| 4,939,138 | A | 7/1990 | D'Ambra et al. |
| 7,304,064 | B2 | 12/2007 | Cowley et al. |

FOREIGN PATENT DOCUMENTS

| EP | 0 393 766 | 10/1990 |
| EP | 1243268 | 9/2002 |
| WO | WO 90/07505 A1 | 7/1990 |
| WO | WO 98/06715 | 2/1998 |
| WO | WO 99/57106 A1 | 11/1999 |
| WO | WO 01/43746 | 6/2001 |
| WO | WO 01/58869 A2 | 8/2001 |
| WO | WO 04/000832 | 12/2003 |

OTHER PUBLICATIONS

Hogenauer et al. Expert Opin.Ther.Patents vol. 17,p. 1457-1476 (2007).*
International Search Report No. PCT/EP2004/053421 dated Apr. 25, 2005.

Duflos, M. et al., "N-Pyridinyl-indole-3-(alkyl)carboxamides and derivatives as potential systemic and topical inflammation inhibitors," Eur. J. Med. Chem., vol. 36, No. 6 (2001), pp. 545-553.
Jung, Michel E., et al., "Organic Chemistry of L-Tryosine," *J. Org. Chem.*, 1985, 50, pp. 4909-4913.
Howlett, A. C. et al., "International Union of Pharmacology. XXVII. Classification of Cannabinoid Receptors," Pharmacological Reviews, Rev., vol. 54, No. 2 (2002) pp. 161-202.
Iversen, L. et al., "Cannabinoids: a real prospect for pain relief?," Current Opinion in Pharmacology, vol. 2 (2002) pp. 50-55.
Eissenstat, M. A. et al., "Aminoalkylindoles: Structure-Activity Relationships of Novel Cannabinoid Mimetics," J. Med. Chem., vol. 38 (1995), pp. 3094-3105.
Robinson, B., "Recent Studies on the Fischer Indole Synthesis," Chem. Rev., vol. 69 (1963) pp. 227-250.

(Continued)

*Primary Examiner*—Emily Bernhardt
(74) *Attorney, Agent, or Firm*—Susan Hess

(57) ABSTRACT

The invention relates to tricyclic 1-[(indol-3-yl)carbonyl]piperazine derivative having the general Formula (I) wherein X is $CH_2$, O or S; R represents 1-3 substituents independently selected from H, $(C_{1-4})$alkyl, $(C_{1-4})$alkyloxy and halogen; $R_1$ is $(C_{5-8})$cycloalkyl; $R_2$ is H or $(C_{1-4})$alkyl; $R_3$, $R_3'$, $R_4$, $R_4'$, $R_5$, $R_5'$ and $R_6'$ are independently hydrogen or $(C_{1-4})$-alkyl, optionally substituted with $(C_{1-4})$alkyloxy, OH or halogen; $R_6$ is hydrogen or $(C_{1-4})$alkyl, optionally substituted with $(C_{1-4})$alkyloxy, OH or halogen; or $R_6$ forms together with $R_7$ a 4-7 membered saturated heterocyclic ring, optionally containing a further heteroatom selected from O and S; $R_7$ forms together with $R_6$ a 4-7 membered saturated heterocyclic ring, optionally containing a further heteroatom selected from O and S; or $R_7$ is H, $(C_{1-4})$alkyl or $(C_{3-5})$cycloalkyl, the alkyl groups being optionally substituted with OH, halogen or $(C_{1-4})$alkyloxy; or a pharmaceutically acceptable salt thereof. The invention also relates to pharmaceutical compositions comprising said tricyclic 1-[(indol-3-yl)carbonyl]piperazine derivatives, and to the use of these derivatives in the treatment of pain, such as peri-operative pain, chronic pain neuropathic pain, cancer pain, and pain and spasticity associated with multiple sclerosis.

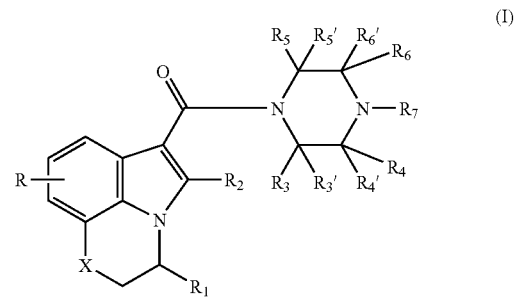

(I)

9 Claims, No Drawings

OTHER PUBLICATIONS van Wijngaarden, I. et al., "Development of High-Affinity 5-$HT_3$ Receptor Antagonists. Structure-Affinity Relationships of Novel 1,7-Annelated Indole Derivatives," J. Med. Chem., vol. 36 (1993) pp. 3693-3699.

Hwu, J. R. et al., "Novel Methods for the Synthesis of Functionalized Indoles from Arylhydroxylamines and Activated Acetylenes," J. Org. Chem., vol. 59 (1994) pp. 1577-1582.

Stratowa, C. et al., "Use of a luciferase reporter system for characterizing G-protein-linked receptors," Current Opinion in Biotechnology, vol. 6 (1995) pp. 574-581.

Dinsmore, Christopher J., et al., "Recent Advances in the Synthesis of Diketopiperazines," *Tetrahedron 58* (2002), pp. 3297-3312.

Battaglia, et al., "Indole amide derivatives: synthesis, structure-activity relationships and molecular modelling studies of a new series of histamine $H_1$-receptor antagonists", Eur. J. Med. Chem. vol. 34, pp. 93-105 (1999).

Jacobsen, et al., "Piperazine Imidazo[1,5-α]quinoxaline Ureas as High-Affinity $GABA_A$ Ligands of Dual Functionality", J. Med. Chem., vol. 42, pp. 1123-1144 (1999).

Peterson, et al., "Decarbonylation of 3-Indoleglyoxalyl Chloride", J. Org. Chem., vol. 23, pp. 303-304 (1958).

Swain, et al., "Novel 5-$HT_3$ Antagonists. Indole Oxadiazoles", J. Med. Chem., vol. 34, pp. 140-151 (1991).

Török, et al., "General Synthesis of Methyl- and Dimethylcyclobutanes from Simple 1,3-Diols by Phase Transfer Catalysis", J. Chem. Soc. Perkin Trans., vol. 1, pp. 801-804 (1993).

An International Search Report, dated Oct. 10, 2003, which was issued during the prosecution of International Application No. PCT/EP2003/50226.

* cited by examiner

TRICYCLIC 1-[(INDOL-3-YL)CARBONYL]PIPERAZINE DERIVATIVES AS CANNABINOID CB1 RECEPTOR AGONISTS

This case was filed under the Patent Cooperation Treaty on Dec. 13, 2004 and claims priority of U.S. provisional application Ser. No. 60/530,528 filed on Dec. 17, 2003.

The present invention relates to tricyclic 1-[(indol-3-yl)carbonyl]piperazine derivatives, to pharmaceutical compositions comprising the same and to the use of these tricyclic 1-[(indol-3-yl)carbonyl]piperazine derivatives in therapy, especially in the treatment of pain.

Pain treatment is often limited by the side effects of currently available medication. For moderate to severe pain, opioids are widely used. These agents are cheap and effective but suffer from serious and potentially life-threatening side effects, most notably respiratory depression and muscle rigidity. In addition, the doses of opioids which can be administered are limited by nausea, emesis, constipation, pruritis and urinary retention, often resulting in patients electing to receive sub-optimal pain control rather than suffer these distressing side effects. Furthermore, these side effects often result in patients requiring extended hospitalisation. Opioids are highly addictive and are scheduled drugs in many territories. There is therefore a demand for new analgesics that have an improved side effect profile compared to currently used products, at equi-analgesic doses.

Evidence is accumulating that cannabinoid agonists have potential as analgesic and anti-inflammatory agents. Two types of cannabinoid receptors are implicated, the cannabinoid CB1 receptor, which is located primarily in the central nervous system but which is also expressed by peripheral neurones and to a lower extent in other peripheral tissues, and the cannabinoid CB2 receptor, which is mostly located in immune cells (Howlett, A. C. et al.: International Union of Pharmacology. XXVII. Classification of Cannabinoid Receptors. *Pharmacol. Rev.* 54, 161-202, 2002). While the CB2 receptor has been implicated in modulating the immune and anti-inflammatory response of cannabinoids, cannabinoid receptor agonists, especially those acting at the CB1 receptor have recently been suggested as useful in the treatment of pain (see Iversen, L. and Chapman, V. *Current Opinion in Pharmacology*, 2, 50-55, 2002 and references therein). WIN 55,212-2, the mesylate salt of (R)-(+)-[2,3-dihydro-5-methyl-[(morpholinyl)methyl]pyrrolo[1,2,3-de]-1,4-benzoxazinyl]-(1-naphthalenyl)methanone was disclosed in U.S. Pat. No. 4,939,138 (Sterling Drug Inc.) as an analgesic agent. The compound is the prototype of aminoalkylindoles (Eissenstat et al., *J. Med. Chem.* 38, 3094-3105, 1995), which are potent cannabinoid CB1 receptor agonists that can produce antinociception with equivalent efficacy to morphine in animal models of acute pain, persistent inflammatory pain and neuropathic pain.

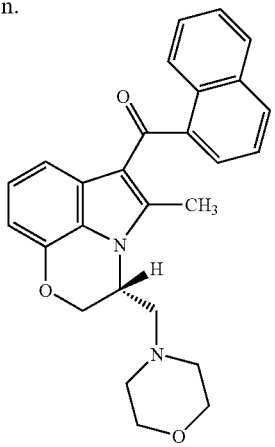

WIN5521-2 (mesylate salt)

Structurally closely related pyrrolo[1,2,3-de]-1,4-benzoxazine carboxamide derivatives have been disclosed in WO 2001/58869 (Bristol-Myers Squibb Comp.) as cannabinoid receptor modulators useful for the treatment of respiratory diseases. Similar tricyclic 3-carboxamido-indole derivatives have been disclosed as 5-HT receptor antagonists in EP 0 393 766 (Duphar Intern. Res. B.V.).

The known cannabinoid agonists are in general highly lipophilic and insoluble in water. There is a thus a need for cannabinoid agonists with improved properties for use as therapeutic agents.

To this end the present invention provides tricyclic 1-[(indol-3-yl)carbonyl]piperazine derivatives having the general Formula I Formula 1

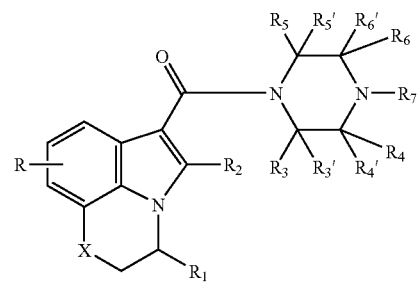

wherein
X is $CH_2$, O or S;
R represents 1-3 substituents independently selected from H, $(C_{1-4})$alkyl, $(C_{1-4})$alkyloxy and halogen;
$R_1$ is $(C_{5-8})$cycloalkyl;
$R_2$ is H or $(C_{1-4})$alkyl;
$R_3$, $R_3'$, $R_4$, $R_4'$, $R_5$, $R_5'$ and $R_6'$ are independently hydrogen or $(C_{1-4})$alkyl, optionally substituted with $(C_{1-4})$alkyloxy, OH or halogen;
$R_6$ is hydrogen or $(C_{1-4})$alkyl, optionally substituted with $(C_{1-4})$alkyloxy, OH or halogen;
or $R_6$ forms together with $R_7$ a 4-7 membered saturated heterocyclic ring, optionally containing a further heteroatom selected from O and S;
$R_7$ forms together with $R_6$ a 4-7 membered saturated heterocyclic ring, optionally containing a further heteroatom selected from O and S; or
$R_7$ is H, $(C_{1-4})$alkyl or $(C_{3-5})$cycloalkyl, the alkyl groups being optionally substituted with $(C_{1-4})$alkyloxy, OH or halogen; or a pharmaceutically acceptable salt thereof, as agonists of the cannabinoid CB1 receptor, which can be used in the treatment of pain such as for example perioperative pain, chronic pain, neuropathic pain, cancer pain and pain and spasticity associated with multiple sclerosis.

The tricyclic core structures of the 1-[(indol-3-yl)carbonyl]piperazine derivatives of the invention are 2,3-dihydropyrrolo[3,2,1-ij]quinoline, where X is $CH_2$; 2,3-dihydro-pyrrolo-[1,2,3-de]-1,4-benzoxazine, where X is oxygen and 2,3-dihydro-pyrrolo[1,2,3-de]-1,4-benzothiazine, where X is sulfur.

The compounds of the invention where X is oxygen are generically described in WO 2001/58869 (supra) as cannabinoid receptor modulators for treating respiratory disease. These modulators are preferentially identified therein as CB2 receptor modulators. The 2,3-dihydro-pyrrolo[1,2,3-de]-1,4-benzoxazine derivatives disclosed in WO 2001/58869 are characterized by the presence of a (4-morpholinyl)methyl side chain attached in the 3-position of the benzoxazine ring. The tricyclic 1-[(indol-3-yl)carbonyl]piperazine derivatives of the invention are distinguished from those of WO 2001/58869 by having a ($C_{5-8}$)cycloalkyl side chain at the corresponding position, a feature that provides compounds having CB1 agonist activity.

The term ($C_{1-4}$)alkyl as used in the definition of Formula I means a branched or unbranched alkyl group having 1-4 carbon atoms, like butyl, isobutyl, tertiary butyl, propyl, isopropyl, ethyl and methyl.

In the term ($C_{1-4}$)alkyloxy, ($C_{1-4}$)alkyl has the meaning as defined above.

The term ($C_{5-8}$)cycloalkyl means a saturated cyclic alkyl group having 5-8 carbon atoms, and can thus represent cyclopentyl, cyclohexyl, cycloheptyl or cyclooctyl.

The term halogen means F, Cl, Br or I

In the definition of Formula I, $R_6$ can form together with $R_7$ a 4-7 membered saturated heterocyclic ring, which means that $R_6$ together with the carbon atom to which it is bound and $R_7$ together with the nitrogen atom to which it is bound complete a 4-7 membered saturated ring, such as an azetidine, a pyrrolidine, a piperidine, or a 1H-azepine ring. Such rings may contain an additional O or S-heteroatom to form rings such as a morpholine, a thiomorpholine, a tetrahydrothiazole- or isothiazole ring.

There is a preference for tricyclic 1-[(indol-3-yl)carbonyl]piperazine derivatives of Formula I wherein R is H and $R_1$ is cyclopentyl or cyclohexyl.

Especially preferred are the tricyclic 1-[(indol-3-yl)carbonyl]piperazine derivatives of Formula I wherein R, $R_2$, $R_3$, $R_3'$, $R_4'$, $R_5$, $R_5'$ and $R_6'$ are H; $R_4$, $R_6$ and $R_7$ are independently H or ($C_{1-4}$)alkyl; or $R_6$ forms together with $R_7$ a 5- or 6-membered saturated heterocyclic ring and $R_4$ is H or ($C_{1-4}$)alkyl.

In the case where X is O, there is a further preference for those isomers in which the stereochemistry at the 3-position of the benzoxazine ring is (R).

The tricyclic 1-[(indol-3-yl)carbonyl]piperazine derivatives of the invention may be prepared by methods known in the art of organic chemistry in general.

Tricyclic 1-[(indol-3-yl)carbonyl]piperazines of Formula I can for instance be prepared from the condensation of a compound of Formula II, wherein R, $R_1$, $R_2$ and X have the meaning as previously defined and C(O)Y represents a carboxylic acid or an activated derivative thereof, such as a carboxylic acid ester or a carboxylic acid halide, preferably a chloride or a bromide, with a compound of Formula III where $R_3$-$R_7$ have the meaning as previously defined. When $R_7$ in compounds of Formula III represents hydrogen, the nitrogen atom to which it is attached may have to be temporarily protected during the condensation reaction. Suitable protecting groups for functional groups which are to be temporarily protected during syntheses are known in the art, for example from Wuts, P. G. M. and Greene, T. W.: *Protective Groups in Organic Synthesis*, Third Edition, Wiley, New York, 1999. When C(O)Y represents a carboxylic acid (i.e., Y is hydroxy) the condensation reaction can be effected with the aid of a coupling reagent, such as for example carbonyl diimidazole, dicyclohexylcarbodiimide and the like, in a solvent such as dimethylformamide or dichloromethane. When C(O)Y represents a carboxylic acid halide (i.e., Y is halide) the condensation with the amine derivative of Formula III can be carried out in the presence of a base, for example triethylamine, in a solvent such as dichloromethane.

When C(O)Y represents a carboxylic acid ester, a direct condensation with the amine derivative of Formula III can be carried out at an elevated temperature.

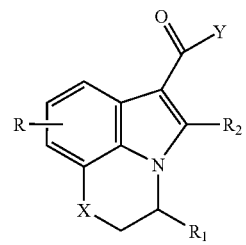

Formula II

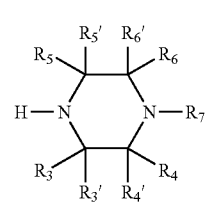

Formula III

Compounds of Formula III can be obtained from commercial sources, prepared by literature procedures or modifications of literature procedures known to those persons skilled in the art. For example, compounds of Formula III can be prepared by reduction of a diketopiperazine, using a reducing agent such as lithium aluminium hydride or borane-tetrahydrofuran complex as described by M. E. Jung and J. C. Rohloff (*J. Org. Chem.* 50, 4909-4913, 1985). Diketopiperazines can be prepared by a variety of routes, as described by C. J. Dinsmore and D. C. Bershore (*Tetrahedron* 58, 3297-3312, 2002).

Compounds of Formula II can be prepared by literature procedures or modifications of literature procedures known to those persons skilled in the art. For example, compounds of Formula II where C(O)Y represents a carboxylic acid and $R_2$ is ($C_{1-4}$)alkyl can be prepared by alkylation of compounds of Formula II where C(O)Y represents a carboxylic acid and $R_2$ is hydrogen, by treatment with at least two equivalents of a strong base, such as n-butyl lithium, followed by treatment with an alkylating agent, such as a ($C_{1-4}$)alkyl halide.

Compounds of Formula II can be prepared by acylation of a compound of Formula IV, using an acylating reagent. For example, compounds of Formula II where Y is hydroxy can be accessed from compounds of Formula IV by treatment with trifluoroacetic anyhydride in a solvent such as dimethylformamide, followed by hydrolysis using aqueous sodium hydroxide at an elevated temperature. Compounds of Formula II where Y is chloride can be prepared by reaction of a compound of Formula IV with oxalyl chloride in a solvent such as 1,1,2,2-tetrachloroethane followed by rearrangement at elevated temperature. Compounds of Formula IV can be prepared from compounds of Formula V using the Fischer indole synthesis (*Chem. Rev.* 69, 227-250, 1969).

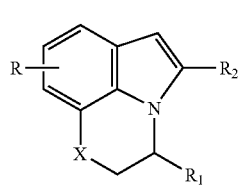

Formula IV

-continued

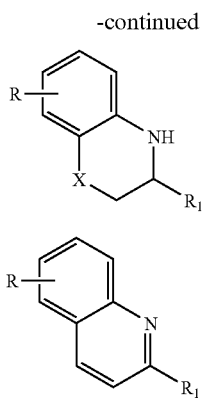

Formula V

Formula VI

Alternatively, compounds of Formula II can be prepared from compounds of Formula V using procedures described by Wijngaarden et al. (*J. Med. Chem.* 36, 3693-3699, 1993) or Hwu et al. (*J. Org. Chem.* 59, 1577-1582, 1994) or modifications of these procedures.

Compounds of Formula V can be prepared by literature procedures or modifications of literature procedures known to those persons skilled in the art. For example compounds of Formula V where X is $CH_2$ can be prepared from compounds of Formula VI by reduction, using a reducing agent such as sodium borohydride in the presence of a catalyst such as nickel (II) chloride. Compounds of Formula VI can for example be prepared by a coupling reaction, such as reaction of a 2-chloroquinoline with a $(C_{5-8})$cycloalkyl Grignard reagent, in the presence of a catalyst such as nickel (II) chloride.

Compounds of Formula V where X is O or S can be prepared by reaction of a compound of Formula VII where X is OH or SH with a compound of Formula VIII to form an ether or thioether, followed by reduction of the nitro group to an amine and reductive cyclisation. The etherification reaction can for example be performed in the presence of a base, such as potassium carbonate, with a catalyst such as potassium iodide. The reduction and cyclisation can for example be carried out using hydrogen gas in the presence of a catalyst such as palladium on charcoal.

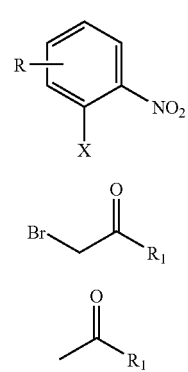

Formula VII

Formula VIII

Formula IX

Compounds of Formula VII and compounds of Formula VIII can be obtained from commercial sources, prepared by literature procedures or modifications of literature procedures known to those persons skilled in the art. For example, compounds of formula VIII can be prepared from compounds of formula IX using a brominating agent such as bromine in a solvent such as methanol.

The skilled person will likewise appreciate that various tricyclic 1-[(indol-3-yl)-carbonyl]piperazine derivatives of Formula I can be obtained by appropriate conversion reactions of functional groups corresponding to certain of the substituents R and $R_3$-$R_7$. For example, compounds of Formula I wherein $R_7$ is $(C_{1-4})$alkyl or $(C_{3-5})$-cycloalkyl, the alkyl groups of which may be substituted with OH, halogen or $(C_{1-4})$-alkyloxy, can be prepared by the reaction of a compound of Formula I wherein $R_7$ is hydrogen with a $(C_{1-4})$alkyl halide or a functionalised $(C_{1-4})$alkyl halide, in the presence of a base such as potassium carbonate.

The tricyclic 1-[(indol-3-yl)carbonyl]piperazine derivatives of Formula I and their salts contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis or chiral separation whereby the pure stereoisomers are obtained are well known in the art, e.g. synthesis with chiral induction or starting from commercially available chiral substrates, or separation of stereoisomers, for example using chromatography on chiral media or by crystallisation with a chiral counter-ion.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid, methane sulfonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a tricyclic 1-[(indol-3-yl)carbonyl]piperazine derivative having the general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The tricyclic 1-[(indol-3-yl)carbonyl]piperazine derivatives of the invention were found to be agonists of the CB1 receptor, as determined in a human CB1 reporter assay using CHO cells. Methods to determine receptor binding as well as in vitro biological activity of cannabinoid receptor modulators are well known in the art. In general, expressed receptor is contacted with the compound to be tested and binding or stimulation or inhibition of a functional response is measured.

To measure a functional response isolated DNA encoding the CB1 receptor gene, preferably the human receptor, is expressed in suitable host cells. Such a cell might be the Chinese Hamster Ovary cell, but other cells are also suitable. Preferably the cells are of mammalian origin.

Methods to construct recombinant CB1 expressing cell lines are well known in the art (Sambrook et al., Molecular Cloning: a Laboratory Manual, Cold Spring Harbor Laboratory Press, Cold Spring Harbor, latest edition). Expression of the receptor is attained by expression of the DNA encoding the desired protein. Techniques for ligation of additional sequences and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed CB1 (or CB2) receptor may be used to measure binding of compound.

For measurement of binding radioactively or fluorescently labelled compounds may be used. The most widely used radiolabelled cannabinoid probe is [$^3$H]CP55940, which has approximately equal affinity for CB1 and CB2 binding sites.

Another assay involves screening for cannabinoid CB1 agonist compounds by determining the second messenger response, such as for example measurement of receptor mediated changes in cAMP or MAPkinase pathways. Thus, such a method involves expression of the CB1 receptor on the cell surface of a host cell and exposing the cell to the test compound. The second messenger response is then measured. The level of second messenger will be reduced or increased, depending on the effect of the test compound upon binding to the receptor.

In addition to direct measurement of e.g. cAMP levels in the exposed cell, cells can be used which in addition to transfection with receptor encoding DNA are also transfected with a second DNA encoding a reporter gene, the expression of which correlates with receptor activation. In general, reporter gene expression might be controlled by any response element reacting to changing levels of second messenger. Suitable reporter genes are e.g. LacZ, alkaline phosphatase, firefly luciferase and green fluorescent protein. The principles of such transactivation assays are well known in the art and are described e.g. in Stratowa, Ch, Himmler, A. and Czemilofsky, A. P., *Curr. Opin. Biotechnol.* 6, 574 (1995). For selecting active agonist compounds on the CB1 receptor the $EC_{50}$ value must be $<10^{-5}$ M, preferably $<10^{-7}$ M.

The compounds may be used in the treatment of pain such as for example peri-operative pain, chronic pain, neuropathic pain, cancer pain and pain and spasticity associated with multiple sclerosis.

Cannabinoid agonists of the invention would also potentially be useful in the treatment of other disorders including multiple sclerosis, spasticity, inflammation, glaucoma, nausea and emesis, loss of appetite, sleep disturbances, respiratory disorders, allergies, epilepsy, migraine, cardiovascular disorders, neurodegenerative disorders, anxiety, traumatic brain injury and stroke.

The compounds could also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is illustrated by the following Examples.

EXAMPLE 1

(R)-3-Cyclohexyl-2,3-dihydro-6-(4-ethylpiperazin-1-ylcarbonyl)pyrrolo[1,2,3-de]-1,4-benzoxazine hydrochloride salt To a solution of D-N-Boc-cyclohexylglycine (25.0 g, 97.2 mmol) in dimethylformamide (200 ml), were added sodium hydrogen carbonate (24.5 g, 291.6 mmol) and methyl iodide (6.66 ml, 106.9 mmol). The mixture was stirred at room temperature for 64 h under nitrogen. The resulting mixture was partitioned between dichloromethane and water. The aqueous layer was extracted with dichloromethane and combined organic layers were washed with brine, dried over sodium sulfate and concentrated. The obtained crystals were washed with n-heptane to afford D-N-Boc-cyclohexylglycine methyl ester (25.65 g, 94.5 mmol).

To a solution of D-N-Boc-cyclohexylglycine methyl ester (25.65 g, 94.5 mmol) in methanol (200 ml) and tetrahydrofuran (100 ml), were added calcium chloride (21.0 g, 189 mmol) and sodium borohydride (14.3 g, 378 mmol). The mixture was stirred at room temperature for 30 min under nitrogen. The resulting mixture was poured into ice water, neutralised with 5 N hydrochloric acid, and partitioned between dichloro-methane and water. The aqueous layer was extracted with dichloromethane and combined organic layers were washed with saturated sodium carbonate solution and brine, dried over sodium sulfate and concentrated. The residue was crystallized from heptane to afford crude (R)-N-Boc-2-cyclohexylethanolamine (29.38 g, 94.5 mmol).

To a mixture of crude (R)-N-Boc-2-cyclohexylethanolamine (29.38 g, 94.5 mmol) and triphenylphosphine (37.2 g, 141.8 mmol) in toluene (150 ml) at 0° C. was added diisopropyl azodicarboxylate (19.5 ml, 99.2 mmol). After stirring for 1 h, 2-bromophenol (12.1 ml, 104.0 mmol) was added to the mixture at 0° C. The reaction mixture was stirred for 2 h at 0° C. and for 20 h at room temperature. The resulting mixture was partitioned between dichloromethane and water. The aqueous layer was extracted with dichloromethane and the combined organic layers were washed with 2 N sodium hydroxide solution and brine, dried over sodium sulfate and concentrated. The residue was purified by flash chromatography eluting with 0-10% (v/v) ethyl acetate in heptane to afford (R)-2-(2-tert-butoxycarbonylamino-2-cyclohexylethoxy)-bromobenzene (12.80 g, 32.1 mmol).

A mixture of (R)-2-(2-tert-butoxycarbonylamino-2-cyclohexylethoxy)bromobenzene (500 mg, 1.26 mmol), tetrakis(triphenylphosphine)palladium(0) (146 mg, 0.126 mmol) and sodium tert-butoxide (181 mg 1.88 mmol) in toluene (4.0 ml) was exposed to microwave irradiation for 10 min at 120° C. The resulting mixture was partitioned between dichloromethane and water. The aqueous layer was extracted with dichloro-methane and combined organic layers were washed with brine, dried over sodium sulfate and concentrated. The residue was purified by flash chromatography eluting with 0-17% (v/v) ethyl acetate in heptane to afford (R)-4-tert-butoxycarbonyl-3-cyclo-hexyl-3,4-dihydro-2H-1,4-benzoxazine (270 mg, 0.85 mmol). This reaction was repeated 13 times on the same scale to afford the same intermediate (a total of 3.98 g, 12.5 mmol).

A mixture of (R)-4-tert-butoxycarbonyl-3-cyclohexyl-3,4-dihydro-2H-1,4-benzoxazine (3.98 g, 12.5 mmol), 5 N hydrochloric acid (10 ml) and ethanol (10 ml) was stirred at 70° C. for 50 min. Ethanol was removed in vacuo and the residue was partitioned between dichloromethane and 2 N sodium hydroxide solution. The aqueous layer was extracted with dichloromethane and combined organic layers were washed with brine, dried over sodium sulfate and concentrated to afford (R)-3-cyclohexyl-3,4-dihydro-2H-1,4-benzoxazine (2.72 g, 12.5 mmol).

(R)-3-cyclohexyl-3,4-dihydro-2H-1,4-benzoxazine (2.72 g, 12.5 mmol) was dissolved in N,N-dimethylformamide (20 ml) and a solution of sodium nitrite (949 mg, 13.8 mmol) in water (3.0 ml) was added at 0° C. Then, 5 N hydrochloric acid (6.0 ml) was added at 0° C. The reaction mixture was stirred at 0° C. for 1 h, then partitioned between ethyl acetate and water. The aqueous layer was extracted with ethyl acetate and the combined organic layers were washed with brine, dried over sodium sulfate and concentrated. The obtained residue was dissolved in diethyl ether (50 ml), and lithium aluminum hydride in tetrahydrofuran (1.0 M; 9.51 ml, 9.51 mmol) was added at 0° C. The reaction mixture was stirred at 0° C. for 1 h, then quenched with ice water. Ethyl acetate was added to the mixture and the mixture was filtered through a plug of Celite, and the filter cake washed with ethyl acetate. The filtrate was partitioned and the aqueous layer extracted with ethyl acetate. The combined organic layers were washed with brine, dried over sodium sulfate and concentrated. The residue was purified by flash chromatography eluting with 0-17% (v/v) ethyl acetate in heptane to afford (R)-4-amino-3-cyclohexyl-3,4-dihydro-2H-1,4-benzoxazine (1.47 g, 6.33 mmol).

Ethyl pyruvate (882 mg, 7.59 mmol) was added to a solution of (R)-4-amino-3-cyclohexyl-3,4-dihydro-2H-1,4-benzoxazine (1.47 g, 6.33 mmol) in ethanol (40 ml). The reaction mixture was stirred at room temperature for 15 min. To the reaction mixture, sulfuric acid (10% v/v in ethanol; 8.0 ml) was added. The reaction mixture was refluxed for 2 h. The mixture was cooled to room temperature and partitioned between ethyl acetate and sodium carbonate solution. The aqueous layer was extracted with ethyl acetate and the combined organic layers washed with brine, dried over sodium sulfate and concentrated. The residue was purified by flash chromatography eluting with 0-10% (v/v) ethyl acetate in heptane to afford ethyl (R)-3-cyclohexyl-2,3-dihydropyrrolo[1,2,3-de]-1,4-benzoxazine-5-carboxylate (1.49 g, 4.76 mmol).

To a solution of ethyl (R)-3-cyclohexyl-2,3-dihydropyrrolo[1,2,3-de]-1,4-benzoxazine-5-carboxylate (1.49 g, 4.76 mmol) in ethanol (50 ml) was added 4 N sodium hydroxide (5.94 ml, 23.8 mmol). The mixture was stirred at 70° C. for 40 min. Ethanol was removed in vacuo, and the residue was neutralised with 2 N hydrochloric acid, and partitioned between dichloromethane and water. The aqueous layer was extracted with dichloromethane and the combined organic layers washed with brine, dried over sodium sulfate and concentrated. The residue was dissolved in quinoline (20 ml), then copper powder (453 mg, 7.13 mmol) was added. The mixture was stirred at 210° C. for 1 h. Ethyl acetate and water were added to the mixture at room temperature, and the mixture was filtered through a plug of Celite, and the filter cake washed with ethyl acetate. The filtrate was acidified with 5 N hydrochloric acid and partitioned. The aqueous layer was extracted with ethyl acetate and the combined organic layers washed with 1 N hydrochloric acid and brine, dried over sodium sulfate and concentrated. The residue was purified by flash chromatography eluting with 0-10% (v/v) ethyl acetate in heptane to afford (R)-3-cyclohexyl-2,3-dihydropyrrolo[1,2,3-de]-1,4-benzoxazine (984 mg, 4.08 mmol).

To a solution of (R)-3-cyclohexyl-2,3-dihydropyrrolo[1,2,3-de]-1,4-benzoxazine (80 mg, 0.33 mmol) in 1,1,2,2-tetrachloroethane (2.0 ml), was added oxalyl chloride (46 mg, 0.36 mmol) with stirring under a stream of nitrogen. The mixture was heated at 120° C. for 1 hour. The mixture was cooled to room temperature and triethylamine (36 mg, 0.36 mmol) and N-ethylpiperazine (45 mg, 0.40 mmol) were added. The mixture was stirred at room temperature for 18 h then partitioned between dichloromethane and water. The aqueous layer was extracted with dichloromethane, and the combined organic layers were washed with brine, dried over $Na_2SO_4$ and concentrated. The resulting brown oil was purified by flash chromatography using 5% (v/v) methanol in dichloromethane as eluent to yield the title compound as the free base. Hydrochloride salt formation was achieved by the addition of hydrogen chloride (2 M solution in diethyl ether, 0.5 ml) to a solution of the free base in diethyl ether (2 ml) and ethanol (1 ml). The solvent was removed in vacuo and the precipitate was dried to afford title compound (1:1 hydrochloride salt) as a solid (70 mg, 0.17 mmol).

$^1$H NMR (400 MHz, $CD_3OD$) δ 1.00-1.40 (6H, m), 1.38 (3H, t, J 7.3), 1.58 (1H, d, J 12.4), 1.62-1.70 (1H, m), 1.70-1.80 (2H, m), 1.80-1.90 (1H, m), 3.10-3.70 (6H, m), 3.25 (2H, q, J 7.3), 4.20-4.60 (4H, m), 4.71 (1H, dd, J 3.0, 12.6), 6.66 (1H, d, J 7.8), 7.08 (1H, t, J 7.8), 7.22 (1H, d, J 7.8), 7.74 (1H, s); EsIMS: m/z=382.2 [M+H]$^+$, 268.2; $[\alpha]_D^{22}$ –18.5° (c=1.4 mg/ml in methanol).

EXAMPLE 2

(R)-3-Cyclohexyl-2,3-dihydro-6-[(S)-octahydro-2H-pyrido[1,2-a]pyrazin-2-ylcarbonyl]-pyrrolo[1,2,3-de]-1,4-benzoxazine hydrochloride salt To a solution of (S)-(+)-1-(tert-butoxycarbonyl)-2-piperidine carboxylic acid (2.00 g, 8.72 mmol) in dichloromethane (30 ml) were added glycine methyl ester hydrochloride (1.09 g, 8.72 mmol), 1-[3-(dimethylamino)propyl]-3-ethyl carbodiimide hydrochloride (2.01 g, 10.46 mmol), 1-hydroxybenzotriazole (1.22 g, 9.04 mmol) and triethylamine (2.43 ml, 17.4 mmol). The mixture was stirred under a stream of nitrogen for 18 h. The resulting mixture was washed with 0.5 M hydrochloric acid (20 ml), water (2×20 ml) and brine (20 ml), dried over sodium sulfate and concentrated to yield (S)-1-(tert-butoxycarbonyl)piperidine-2-carboxyglycine methyl ester as a colourless oil (2.47 g, 8.23 mmol).

(S)-1-(Tert-butoxycarbonyl)piperidine-2-carboxyglycine methyl ester (2.46 g, 8.20 mmol) was dissolved in trifluoroacetic acid (10 ml) and the resulting solution stirred for 1 hour. The trifluoroacetic acid was then removed to yield a colourless oil, which was dissolved in methanol (85 ml) and triethylamine (9.0 ml, 64.6 mmol) added. The resulting mixture was heated under reflux for 4 h. The solution was then concentrated to afford a pale orange oil which was recrystallised from heptane 48%, ether 48%, 2-propanol 4%, to yield (S)-octahydro-1,4-dioxo-2H-pyrido[1,2-a]pyrazine as white crystals (0.66 g, 3.90 mmol).

(S)-Octahydro-1,4-dioxo-2H-pyrido[1,2-a]pyrazine (0.5 g, 2.98 mmol) was added portionwise to a stirred solution of lithium aluminium hydride (1M in tetrahydrofuran; 11.9 ml, 11.9 mmol). The resulting mixture was heated under reflux for 0.5 h. The solution was then cooled to 0° C. and treated dropwise with water (1.35 ml), 1 M sodium hydroxide solution (0.45 ml), then water (1.35 ml). Tetrahydrofuran (10 ml) was added and the solution stirred for 0.5 h, before filtration. The filter cake was washed with tetrahydrofuran (2×5 ml) and the combined filtrate and washings concentrated to yield (S)-octahydro-2H-pyrido[1,2-a]pyrazine as a yellow oil (0.29 g, 2.07 mmol).

To a solution of (R)-3-cyclohexyl-2,3-dihydropyrrolo[1,2,3-de]-1,4-benzoxazine (100 mg, 0.41 mmol) in 1,1,2,2-tetrachloroethane (2.0 ml), was added oxalyl chloride (58 mg, 0.46 mmol) with stirring under a stream of nitrogen. The mixture was heated at 120° C. for 1.5 h. The mixture was cooled to room temperature and triethylamine (46 mg, 0.46 mmol) and (S)-octahydro-2H-pyrido[1,2-a]pyrazine (70 mg, 0.50 mmol) were added. The mixture was stirred at room temperature for 19 h and then partitioned between dichloromethane and water. The aqueous layer was extracted with dichloromethane, and the combined organic layers washed with brine, dried over Na$_2$SO$_4$ and concentrated. The resulting brown oil was purified by flash chromatography eluting with 50% (v/v) ethyl acetate in n-heptane, then 0-17% (v/v) methanol in ethyl acetate to afford the title compound as the free base. Hydrochloride salt formation was achieved by the addition of hydrogen chloride (2 M solution in diethyl ether, 1 ml) to a solution of the free base in diethyl ether (2 ml) and ethanol (2 ml). The solvent was removed in vacuo and the precipitate was dried to afford the title compound (1:1 hydrochloride salt) as a solid (78 mg, 0.18 mmol).

$^1$H NMR (400 MHz, CD$_3$OD) δ 1.00-1.35 (6H, m), 1.50-2.05 (11H, m), 3.00-3.10 (1H, m), 3.10-3.30 (3H, m), 3.40-3.55 (3H, m), 4.20-4.30 (2H, m), 4.50-4.70 (2H, m), 4.71 (1H, dd, J 3.0, 12.6), 6.67 (1H, d, J 7.2), 7.08 (1H, t, J 7.8), 7.21 (1H, d, J 7.2), 7.74 (1H, s); EsIMS: m/z=408.2 [M+H]$^+$, 268.2; $[\alpha]_D^{22}$ –27.5° (c=5.8 mg/ml in methanol).

EXAMPLE 3

(S)-3-Cyclohexyl-2,3-dihydro-6-[(S)-octahydro-2H-pyrido[1,2-a]pyrazin-2-yl carbonyl]pyrrolo[1,2,3-de]-1,4-benzoxazine hydrochloride salt The title compound was prepared using the procedure described under Example 2 using (S)-3-cyclohexyl-2,3-dihydropyrrolo[1,2,3-de]-1,4-benzoxazine, which was prepared from L-N-Boc-cyclohexylglycine according to the procedure of Example 1.

$^1$H NMR (400 MHz, CD$_3$OD) δ 1.00-1.35 (6H, m), 1.50-2.05 (11H, m), 3.05 (1H, t, J 10.4), 3.10-3.30 (3H, m), 3.40-3.55 (3H, m), 4.20-4.30 (2H, m), 4.30-4.60 (2H, m), 4.71 (1H, dd, J 3.0, 12.6), 6.66 (1H, d, J 8.0), 7.08 (1H, t, J 8.0), 7.22 (1H d, J 8.0), 7.73 (1H, s); EsIMS: m/z=408.2 [M+H]$^+$, 268.2; $[\alpha]_D^{22}$ +14.4° (c=1.3 mg/ml in methanol).

EXAMPLE 4

(R)-3-Cyclohexyl-2,3-dihydro-6-[(S)-3,4-dimethylpiperazin-1-ylcarbonyl]pyrrolo[1,2,3-de]-1,4-benzoxazine hydrochloride salt To a solution of (R)-3-cyclohexyl-2,3-dihydropyrrolo[1,2,3-de]-1,4-benzoxazine (600 mg, 2.49 mmol) in N,N-dimethylformamide (5.0 ml) at 0° C. was added trifluoroacetic anhydride (0.311 ml, 2.73 mmol). The mixture was stirred at room temperature for 5 h, then partitioned between dichloromethane and water. The aqueous layer was extracted with dichloromethane, and combined organic layers were washed with brine, dried over Na$_2$SO$_4$ and concentrated. The residue was purified by flash chromatography eluting with 0-25% (v/v) ethyl acetate in heptane to afford (R)-3-cyclohexyl-6-trifluoromethylcarbonyl-2,3-dihydropyrrolo[1,2,3-de]-1,4-benzoxazine (628 mg, 1.86 mmol).

To a solution of (R)-3-cyclohexyl-6-trifluoromethylcarbonyl-2,3-dihydropyrrolo[1,2,3-de]-1,4-benzoxazine (628 mg, 1.86 mmol) in 1,4-dioxane (20 ml) was added 4 N NaOH (5.0 ml). The mixture was refluxed for 42 h, then acidified to pH 1 using 5 N hydrochloric acid and partitioned between dichloromethane and water. The aqueous layer was extracted with dichloromethane, and combined organic layers were washed with brine, dried over Na$_2$SO$_4$ and concentrated to afford crude (R)-3-cyclohexyl-2,3-dihydropyrrolo[1,2,3-de]-1,4-benzoxazine-6-carboxylic acid (572 mg).

To a solution of (R)-3-cyclohexyl-2,3-dihydropyrrolo[1,2,3-de]-1,4-benzoxazine-6-carboxylic acid (120 mg, 0.421 mmol) and (S)-1,2-dimethylpiperazine (62 mg, 0.547 mmol) in N,N-dimethylformamide (3.0 ml) was added 1-(3-dimethylaminopropyl-3-ethylcarbodiimide (97 mg, 0.505 mmol) and 1-hydroxy benzotriazole (68 mg, 0.505 mmol). The mixture was stirred at room temperature for 18 h, then partitioned between dichloromethane and water. The aqueous layer was extracted with dichloromethane, and combined organic layers were washed with brine, dried over Na$_2$SO$_4$ and concentrated. The residue was purified by flash chromatography eluting with 0-20% (v/v) methanol in ethyl acetate to afford the title compound as the free base. Hydrochloride salt formation was achieved by the addition of hydrogen chloride (2

M solution in diethyl ether; 0.5 ml) to a solution of the free base in diethyl ether (2 ml) and ethanol (1 ml). The solvent was removed in vacuo and the precipitate was dried to afford title compound (1:1 hydrochloride salt) as a solid (84 mg, 0.20 mmol).

$^1$H NMR (400 MHz, CD$_3$OD) δ 1.00-1.35 (5H, m), 1.39 (3H, d, J 4.8), 1.58 (1H, d, J 12.0), 1.60-1.70 (1H, m), 1.70-1.82 (3H, m), 1.82-1.90 (1H, m), 2.96 (3H, s), 3.20-3.70 (5H, m), 4.20-4.30 (2H, m), 4.40-4.70 (2H, m), 4.71 (1H, d, J 10.0), 6.67 (1H, d, J 8.2), 7.08 (1H, t, J 8.2), 7.21 (1H, d, J 8.2), 7.74 (1H, s); EsIMS: m/z=382.1 [M+H]$^+$, 268.1.

EXAMPLE 5

The method of Example 4 was further used to prepare the following compounds:

5A: (R)-3-Cyclohexyl-2,3-dihydro-6-[(s)-3-methylpiperazin-1-ylcarbonyl]pyrrolo-[1,2,3-de]-1,4-benzoxazine hydrochloride salt was prepared using (S)-2-methylpiperazine instead of (S)-1,2-dimethylpiperazine.

EsIMS: m/z=368 [M+H]$^+$, 267.8; [α]$_D^{22}$–44.4° (c=2.3 mg/ml in methanol).

5B: (R)-3-Cyclohexyl-2,3-dihydro-6-[(cis)-3,5-dimethylpiperazin-1-ylcarbonyl]pyrrolo[1,2,3-de]-1,4-benzoxazine hydrochloride salt was prepared using cis-2,6-dimethylpiperazine instead of (S)-1,2-dimethylpiperazine.

EsIMS: m/z=382.1 [M+H]$^+$, 267.6; [α]$_D^{22}$–19.6° (c=2.8 mg/ml in methanol).

5C: (R)-3-Cyclohexyl-2,3-dihydro-6-[4-methylpirerazin-1-ylcarbonyl]pyrrolo[1,2,3-de]-1,4-benzoxazine hydrochloride salt was prepared using N-methylpiperazine instead of (S)-1,2-dimethylpiperazine.

EsIMS: m/z=368 [M+H]$^+$, 268; [α]$_D^{22}$–20.30° (c=3.0 mg/ml in methanol).

EXAMPLE 6

(R)-3-Cyclohexyl-2,3-dihydro-6-[(cis)-2,6-dimethylpiperazin-1-ylcarbonyl]pyrrolo-[1,2,3-de]-1,4-benzoxazine hydrochloride salt To a solution of (cis)-2,6-dimethylpiperazine (900 mg, 8.49 mmol) and sodium bicarbonate (0.2 ml of saturated solution) in THF (5 ml) was added benzyl bromide (1.02 ml, 8.49 mmol). The mixture was exposed to microwave irradiation at 80° C. for 15 minutes. The solvent was removed in vacuo and the residue was washed with sodium bicarbonate solution and extracted with dichloromethane. The residue was purified by flash chromatography eluting with 5-10% (v/v) methanol in dichloro-methane to afford 1-N-benzyl-(cis)-3,5-dimethylpiperazine as a clear oil (900 mg, 4.40 mmol).

To a solution of (R)-3-cyclohexyl-2,3-dihydropyrrolo[1,2,3-de]-1,4-benzoxazine-6-carboxylic acid (362 mg, 1.23 mmol) in dichloromethane (20 ml) was added oxalyl chloride (0.215 ml, 2.46 mmol). The deep blue mixture was stirred at room temperature for 2 h and then the solvent was removed in vacuo to afford (R)-3-cyclohexyl-2,3-dihydropyrrolo[1,2,3-de]-1,4-benzoxazine-6-carboxylic acid chloride (380 mg, 1.23 mmol) as a blue solid.

To a solution of (R)-3-cyclohexyl-2,3-dihydropyrrolo[1,2,3-de]-1,4-benzoxazine-6-carboxylic acid chloride (380 mg, 1.23 mmol) and N,N diisopropyl ethylamine (0.2 ml, 1.3 mmol) in dichloromethane (20 ml) was added 1-N-benzyl-(cis)3,5-dimethylpiperazine (250 mg, 1.2 mmol) in dichloromethane (5 ml) and the mixture stirred for 16 h at room temperature. The mixture was partitioned between sodium bicarbonate solution and dichloromethane. The organic layer was separated and the solvent removed in vacuo. The residue was purified by flash chromatography eluting with 0-5% (v/v) methanol in dichloromethane. Hydrochloride salt formation was achieved by the addition of hydrogen chloride (2 M solution in diethyl ether; 2 ml) to the free base in dichloromethane (1 ml). The precipitate was filtered and dried to afford (R)-3-cyclohexyl-2,3-dihydro-6-[(cis)-4-benzyl-2,6-dimethylpiperazin-1-yl-carbonyl]pyrrolo[1,2,3-de]-1,4-benzoxazine hydrochloride salt as a light blue powder (240 mg, 0.51 mmol).

To a solution of (R)-3-cyclohexyl-2,3-dihydro-6-[(cis)-4-benzyl-2,6-dimethylpiperazin-1-ylcarbonyl]pyrrolo[1,2,3-de]-1,4-benzoxazine hydrochloride salt (200 mg, 0.42 mmol) in ethanol (5 ml) was added 10% palladium on charcoal (10 mg). The mixture was stirred under a hydrogen atmosphere for 16 h at room temperature. The mixture was filtered and the solvent removed in vacuo to afford the title compound as a white solid (100 mg, 0.26 mmol).

$^1$H NMR (400 Hz, CD$_3$OD) δ1.03-1.39 (5H, m), 1.49 (6H, d, J 7.2), 1.55-1.87 (6H, m), 3.47 (4H, m), 4.29 (2H, m), 4.72 (1H, d, J 9.8), 4.80 (2H, m), 6.66 (1H, d, J 7.5), 7.09 (1H, m, J 7.7), 7.19 (1H, d, J 8.9), 7.66 (1H, s); EsIMS: m/z=382.3 [M+H]$^+$, 268; [α]$_D^{22}$–17.0° (c=2.4 mg/ml in methanol).

EXAMPLE 7

(R)-3-Cyclohexyl-2,3-dihydro-6-[(cis)-3,4,5-trimethylpiperazin-1-ylcarbonyl]pyrrolo[1,2,3-de]-1,4-benzoxazine hydrochloride salt To a solution of (R)-3-cyclohexyl-2,3-dihydro-6-[(cis)-3,5-dimethylpiperazin-1-yl-carbonyl]pyrrolo[1,2,3-de]-1,4-benzoxazine hydrochloride salt (100 mg, 0.26 mmol) in ethanol (10 ml) was added formaldehyde (37% in water; 1 ml, 12.5 mmol) and sodium triacetoxyborohydride (200 mg, 0.93 mmol). The mixture was stirred at room temperature for 30 minutes. The solvent was removed in vacuo. The residue was purified by flash chromatography eluting with 1-10% (v/v) methanol in dichloro-methane to afford the title compound as the free base. Hydrochloride salt formation was achieved by the addition of hydrogen chloride (2 M solution in diethyl ether; 2 ml) to the free base in dichloromethane (1 ml). The precipitate was filtered and dried to afford the title compound (1:1 hydrochloride salt). EsIMS: m/z=396.1 [M+H]$^+$, 268; [α]$_D^{22}$–19.6° (c=2.1 mg/ml in methanol).

EXAMPLE 8

(R)-3-Cyclohexyl-2,3-dihydro-6-[(cis)-3,5-dimethyl-4-ethylpiperazin-1-ylcarbonyl]-pyrrolo[1,2,3-de]-1,4-benzoxazine hydrochloride salt The title compound was prepared following the procedure described under Example 7 using acetaldehyde instead of formaldehyde. EsIMS: m/z=410.3 [M+H]$^+$, 268; [α]$_D^{22}$–17.8° (c=2.0 mg/ml in methanol).

EXAMPLE 9

(R)-3-Cyclohexyl-2,3-dihydro-6-[(cis)-3,5-dimethyl-4-(2-hydroxyethyl)piperazin-1-ylcarbonyl]pyrrolo[1,2,3-de]-1,4-benzoxazine hydrochloride salt To a solution of (R)-3-cyclohexyl-2,3-dihydro-6-[(cis)-3,5-dimethylpiperazin-1-ylcarbonyl]pyrrolo[1,2,3-de]-1,4-benzoxazine hydrochloride salt (120 mg, 0.31 mmol) in acetonitrile (3 ml) was added 2-bromoethanol (0.024 ml, 0.34 mmol). The mixture was exposed to microwave irradiation for 30 minutes at 150° C. The mixture was filtered and the solvent removed in vacuo. The residue was purified using HPLC (Waters Xterra [RP18, 5 µm] 30 mm×10 mm column, 10-100% [v/v] acetonitrile in water over a 25 minute gradient, 0.1% triflouroacetic acid buffer, detected by UV at 254 nm) to afford the title compound as a trifluoroacetic acid (TFA) salt. Hydrochloride salt formation was achieved by the addition of hydrogen chloride (2 M solution in diethyl ether; 2 ml) to the TFA salt in dichloromethane (1 ml). The precipitate was filtered and dried to afford the title compound (20 mg, 0.04 mmol).

$^1$H NMR (400 Hz, CD$_3$OD) δ 1.01-1.39 (5H, m), 1.44 (6H, d, J 5.3), 1.56-1.85 (6H, m), 3.32 (2H, d, J 14.2), 3.54 (2H, s), 3.72 (2H, m), 3.82 (0.5H, m), 3.93 (1.5H, d, J 4.5), 4.24-4.28 (3H, m), 4.36-4.40 (0.5H, d, J 11.6), 4.52 (1.5H, d, J 13.1), 4.69 (1H, d, J 10.1), 6.66 (1H, d, J 7.5), 7.06-7.10 (1H, m) 7.20 (1H, d, J 8.0), 7.75 (1H, s); EsIMS: m/z=426.1 [M+H]$^+$, 268; $[\alpha]_D^{22}$ –18.3° (c=2.2 mg/ml in methanol).

EXAMPLE 10

(R)-3-Cyclohexyl-2,3-dihydro-6-[(cis)-3,5-dimethyl-4-(2-methoxyethyl)piperazin-1-yl-carbonyl]pyrrolo[1,2,3-de]-1,4-benzoxazine hydrochloride salt The title compound was prepared using the procedure described under Example 9 using 2-bromoethyl methyl ether instead of 2-bromoethanol.

EsIMS: m/z=440 [M+H]$^+$, 268; $[\alpha]_D^{22}$ –20.8° (c=2.5 mg/ml in methanol).

EXAMPLE 11

(rac)-4-Cyclopentyl-5,6-dihydro-1-(4-ethylpiperazin-1-ylcarbonyl)-4H-pyrrolo[3,2,1-ij]-quinoline hydrochloride salt To a solution of 2-chloroquinoline (8.2 g, 50 mmol) and [1,2-bis(diphenylphosphino)-ethane]dichloronickel(II) (200 mg, 0.38 mmol) in diethyl ether (20 ml) cooled in a ice/methanol bath was added cyclopentylmagnesium bromide (2 M solution in diethyl ether; 25.5 ml, 51 mmol) over a period of 15 minutes. The resulting brown solution was then stirred for 30 minutes, the ice bath removed and the mixture stirred for a further 10 minutes. The reaction mixture was then re-cooled to 0° C. and a saturated ammonium chloride solution (40 ml) added slowly. The resulting reaction mixture was poured into a separating funnel and further diluted with diethyl ether (60 ml) and saturated ammonium chloride solution (60 ml). The organics were separated and the aqueous layer washed with diethyl ether (2×100 ml). The combined organics were dried (MgSO$_4$), filtered and the solvent removed in vacuo to leave 2-cyclopentylquinoline (9.98 g, 50.4 mmol) as an oil.

To a solution of 2-cyclopentylquinoline (7.95 g, 40.3 mmol) and nickel (II) chloride hexahydrate (1.63 g, 6.85 mmol) in methanol (120 ml) cooled in an ice/methanol bath was added sodium borohydride (6.1 g, 161.2 mmol) portion-wise over 1.5 h. The cooling bath was removed and the reaction stirred for a further 30 minutes. The methanol was then removed in vacuo. To the resulting black precipitate was added 2 M hydrochloric acid (100 ml) and then basified with 10 M potassium hydroxide. The mixture was poured into a separating funnel and extracted with ether (4×200 ml). The combined organic layers were dried (MgSO$_4$), filtered and the solvent removed in vacuo to give 2-cyclopentyl-1,2,3,4-tetrahydroquinoline (7.45 g, 37.1 mmol) as a light brown oil.

To a solution of 2-cyclopentyl-1,2,3,4-tetrahydroquinoline (4.0 g, 20 mmol) in tetrahydrofuran (15 ml) was added ethyl bromopyruvate (~90% purity; 1.38 ml, 9.9 mmol) and the reaction stirred for 15 h. The resulting precipitate was filtered and washed with tetrahydrofuran (20 ml). The filtrate was evaporated in vacuo. The resulting residue was dissolved in tetrahydrofuran (10 ml) and 2-methoxyethanol (10 ml) and the solution added dropwise to a refluxing solution of magnesium (II) chloride (1.05 g, 11 mmol) in 2-methoxyethanol (10 ml). The reaction mixture was refluxed for 2 h and then a further portion of magnesium (II) chloride (1.05 g, 11 mmol) added and refluxing continued overnight. The reaction was cooled and the solvent removed in vacuo. The resulting brown oil was dissolved in dichloromethane (150 ml) and washed with 2 M HCl (50 ml), saturated potassium carbonate (50 ml) and brine (50 ml). The organics were dried (MgSO$_4$), filtered and the solvent removed in vacuo. The resulting oil was purified by flash chromatography using 33-67% (v/v) dichloromethane in heptane to give 4-cyclopentyl-5,6-dihydro-4H-pyrrolo[3,2,1-ij]quinoline-1-carboxylic acid ethyl ester (1.45 g, 4.9 mmol).

To a solution of 4-cyclopentyl-5,6-dihydro-4H-pyrrolo[3,2,1-ij]quinoline-1-carboxylic acid ethyl ester (1.45 g, 4.9 mmol) in water (10 ml) and ethanol (15 ml) was added sodium hydroxide (1.96 g, 49 mmol) and the reaction mixture heated at reflux overnight (~14 h). The reaction was cooled and acidifed with 5 M HCl. The resulting white precipitate was filtered and dried in vacuo to give 4-cyclopentyl-5,6-dihydro-4H-pyrrolo[3,2,1-ij]quinoline-1-carboxylic acid (1.13 g, 4.2 mmol) as a white solid.

To a solution of 4-cyclopentyl-5,6-dihydro-4H-pyrrolo[3,2,1-ij]quinoline-1-carboxylic acid (342 mg, 1.27 mmol) in dichloromethane (20 ml) was added oxalyl chloride (218 µL, 3.18 mmol) and the reaction mixture stirred for 1 h. A further portion of oxalyl chloride (436 µL, 6.36 mmol) was then added and the reaction stirred overnight. Solvent and excess reagents were then removed in vacuo to leave a green solid. The green solid was dissolved in dichloromethane (20 ml) and N-ethylpiperazine (323 µL, 2.54 mmol) was added dropwise. The resulting reaction mixture was stirred for 1 h and then poured into a separating funnel. The organic layer was washed with saturated potassium bicarbonate solution (20 ml) and brine (20 ml), dried (MgSO$_4$) and the solvent removed in vacuo to leave a brown oil. The oil was purified by flash chromatography eluting with 0-5% (v/v) methanol in dichloromethane to give the title compound (400 mg, 1.09 mmol). $^1$H NMR (400 MHz, CD$_3$OD) δ$_H$ 1.31-1.43 (4H, m), 1.45-1.79 (6H, m), 1.87-1.96 (1H, m), 2.05-2.24 (2H, m), 2.30-2.37 (1H, m), 2.90 (1H, dt, J 16.6, 3.9), 3.03-3.20 (3H, m), 3.26 (2H, q, J 7.5), 3.45-3.65 (4H, m), 4.16-4.23 (1H, m), 4.57 (2H, d, J 14.7), 6.99 (1H, d, J 7.1), 7.12 (1H, t, J 8.0), 7.48 (1H, d, J 8.0), 7.76 (1H, s); EsIMS: m/z=366.3 [M+H]$^+$, 252.1.

EXAMPLE 12

The product obtained in Example 11 was subjected to chiral HPLC separation on a Chiracel®OD column (2 cm×25 cm), eluting with isohexane/isopropanol 92/8 (v/v) at 15 ml/min flow rate. The products were detected using a UV detector at a wavelength of 240 nm to give Enantiomer 1; retention time 24.18 minutes; enantiomeric excess >89%, and Enantiomer 2; retention time 33.6 minutes; enantiomeric excess >92%

12A: (+)-4-Cyclopentyl-5,6-dihydro-1-(4-ethylpiperazin-1-ylcarbonyl)-4H-pyrrolo[3,2,1-ij]quinoline hydrochloride salt To a solution of Enantiomer 1 (147 mg, 0.38 mmol) in dichloromethane (5 ml) was added hydrochloric acid (2 M solution in diethyl ether; 0.5 ml). Excess reagent and solvent was removed in vacuo to leave the title compound as a white solid.

EsIMS: m/z=366.1 [M+H]$^+$, 252.1; $[\alpha]_D^{22}$ −25.3° (c=2.4 mg/ml in methanol).

12B: (−)-4-Cylclopentyl-5,6-dihydro-1-(4-ethylpiperazin-1-ylcarbonyl)-4H-pyrrolo[3,2,1-ij]quinoline hydrochloride salt To a solution of Enantiomer 2 (143 mg, 0.38 mmol) in dichloromethane (5 ml) was added hydrochloric acid (2 M solution in diethyl ether; 0.5 ml). Excess reagent and solvent was removed in vacuo to leave the title compound as a white solid.

EsIMS: m/z=366.0 [M+H]$^+$, 252.1; $[\alpha]_D^{22}$ −21.3° (c=2.4 mg/ml in methanol).

EXAMPLE 13

(+)-4-Cyclohexyl-5,6-dihydro-1-(4-ethylpiperazin-1-ylcarbonyl)-4H-pyrrolo[3,2,1-ij]-quinoline hydrochloride salt To a solution of quinoline (11.84 ml, 100 mmol) in chlorobenzene (300 ml) was added sequentially water (300 ml), cyclohexanecarboxylic acid (35.88 g, 280 mmol), silver nitrate (1.36 g, 8.0 mmol), ammonium persulfate (22.82 g, 100 mmol) and trifluoroacetic acid (7.67 g, 100 mmol). The mixture was heated to 140° C. with stirring for 3 h. The mixture was then cooled to room temperature, basified with solid sodium hydroxide and the solvent removed in vacuo. The residue was then subjected to a continuous extraction with isohexane for 18 h, the solvent evaporated under reduced pressure and the residue purified by flash chromatography eluting with 20% (v/v) ethyl acetate in isohexane to afford 2-cyclohexylquinoline as a yellow oil (2.66 g, 12.61 mmol).

A solution of 2-cyclohexylquinoline (2.66 g, 12.61 mmol) in glacial acetic acid (25 ml) was treated with sodium cyanoborohydride (2.38 g, 37.82 mmol) and stirred at room temperature for 4 h and then 40° C. for 18 h. The mixture was then treated with 2 M sodium hydroxide (200 ml), stirred for 30 min and extracted into ethyl acetate (3×100 ml). The combined organic layers were then washed with water (3×100 ml), dried with sodium sulfate, evaporated under reduced pressure and the residue purified by flash chromatography eluting with 0-3% (v/v) ethyl acetate in isohexane to afford 2-cyclohexyl-1,2,3,4-tetrahydroquinoline as a yellow oil (1.61 g, 7.49 mmol).

2-Cyclohexyl-1,2,3,4-tetrahydroquinoline (2.61 g, 12.14 mmol) in ethanol (75 ml) was treated with (R)-(−)-2-hydroxy-5,5-dimethyl-4-phenyl-1,3,2-dioxaphosphorinane-2-oxide (2.94 g, 12.14 mmol) and the mixture stirred at 50° C. until dissolution was complete. The mixture was then evaporated under reduced pressure until the total volume was 30 ml and left to crystallise for 3 h. The suspension was filtered and the colourless precipitate re-crystallised from ethanol to give a colourless crystalline solid (2.1 g). This was treated with saturated sodium carbonate solution (50 ml) and extracted into dichloromethane (2×50 ml). The combined organic layers were then dried with sodium sulfate and evaporated under reduced pressure to afford non-racemic 2-cyclohexyl-1,2,3,4-tetrahydroquinoline as a colourless oil (0.98 g, 4.56 mmol). The enantiomeric excess was determined as 94% by chiral HPLC on a Chiralcel®OJ column, eluting with isohexane/ethanol 97:3 (v/v) at 1 ml/min flow rate. The enantiomers were detected using a UV detector at a wavelength of 230 nm. The enantiomers eluted at retention times of 8.4 min (97%) and 9.4 min (3%).

Following the procedure of Example 1, using the above non-racemic 2-cyclohexyl-1,2,3,4-tetrahydroquinoline instead of (R)-3-cyclohexyl-3,4-dihydro-2H-1,4-benzoxazine, afforded the title compound as a colourless solid (0.05 g, 0.12 mmol). $^1$H NMR (400 MHz, CDCl$_3$) $\delta_H$ 1.05-1.26 (5H, m), 1.48-1.87 (9H, m), 2.01-2.11 (1H, m), 2.30-2.39 (1H, m), 2.70-3.12 (6H, m), 3.44-3.52 (2H, m), 3.96-4.13 (3H, m), 4.53 (2H, d, br, J 14.1), 7.00 (1H, d, J 7.5), 7.16 (1H, t, J 7.4), 7.44 (1H, d, J 8.1), 7.59 (1H, s). EsIMS: m/z 380 [M+H]$^+$, 266; $[\alpha]_D^{22}$ +42.6° (c=2.7 mg/ml in methanol).

EXAMPLE 14

(+)-(4-Cyclohexyl-5,6-dihydro-1-(4-methylpiperazin-1-ylcarbonyl)-4H-pyrrolo[3,2,1-ij]-quinoline hydrochloride salt The title compound was prepared following the procedure described under Example 13 using N-methylpiperazine instead of N-ethylpiperazine. $^1$H NMR (400 MHz, CDCl$_3$) $\delta_H$ 1.05-1.28 (6H, m), 1.51-1.87 (5H, m), 2.02-2.11 (1H, m), 2.31-2.39 (1H, m), 2.76-3.10 (7H, m), 3.41-3.50 (2H, m), 3.92-4.10 (3H, m), 4.55 (2H, d, br, J 13.8), 7.00 (1H, d, J 7.1), 7.16 (1H, t, J 7.0), 7.44 (1H, d, J 8.1), 7.59 (1H, s). EsIMS: m/z 366 [M+H]$^+$, 266; $[\alpha]_D^{22}$ +19.30° (c=1.5 mg/ml in methanol).

EXAMPLE 15

(−)-(4-Cyclohexyl-5,6-dihydro-1-(4-ethylpiperazin-1-ylcarbonyl)-4H-pyrrolo[3,2,1-ij]quinoline hydrochloride salt Non-racemic 2-cyclohexyl-1,2,3,4-tetrahydroquinoline was prepared following the procedure described under Example 13 using (S)-(+)-2-hydroxy-5,5-dimethyl-4-phenyl-1,3,2-dioxaphosphorinane-2-oxide instead of (R)-(−)-2-hydroxy-5,5-dimethyl-4-phenyl-1,3,2-dioxaphosphorinane-2-oxide.

The enantiomeric excess of the 2-cyclohexyl-1,2,3,4-tetrahydroquinoline intermediate was determined as 86% by chiral HPLC on a Chiralcel®OJ column, eluting with isohexane/ethanol 97:3 (v/v) at 1 ml/min flow rate. The enantiomers were detected using a UV detector at a wavelength of 230 nm, at retention times of 8.4 min (7%) and 9.4 min (93%). The title compound was prepared following the procedure of Example 1, using this non-racemic 2-cyclohexyl-1,2,3,4-tetrahydroquinoline instead of (R)-3-cyclohexyl-3,4-dihydro-2H-1,4-benzoxazine. $^1$H NMR (400 MHz, CDCl$_3$) $\delta_H$ 1.05-1.26 (5H, m), 1.48-1.87 (9H, m), 2.01-2.11 (1H, m), 2.30-2.39 (1H, m), 2.70-3.12 (6H, m), 3.44-3.52 (2H, m), 3.96-4.13 (3H, m), 4.53 (2H, d, br, J 14.1), 7.00 (1H, d, J 7.5), 7.16 (1H, t, J 7.4), 7.44 (1H, d, J 8.1), 7.59 (1H, s). EsIMS: m/z 380 [M+H]$^+$, 266; $[\alpha]_D^{22}$ −28.40 (c=1.6 mg/ml in methanol).

EXAMPLE 16

(−)-(4-Cyclohexyl-5,6-dihydro-1-(4-methylpiperazin-1-ylcarbonyl)-4H-pyrrolo[3,2,1-ij]-quinoline hydrochloride salt The title compound was prepared following the procedure described under Example 15 using N-methylpiperazine instead of N-ethylpiperazine.

$^1$H NMR (400 MHz, CDCl$_3$) $\delta_H$ 1.05-1.28 (6H, m), 1.51-1.87 (5H, m), 2.02-2.11 (1H, m), 2.31-2.39 (1H, m), 2.76-3.10 (7H, m), 3.41-3.50 (2H, m), 3.92-4.10 (3H, m), 4.55 (2H, d, br, J 13.8), 7.00 (1H, d, J 7.1), 7.16 (1H, t, J 7.0), 7.44 (1H, d, J 8.1), 7.59 (1H, s). EsIMS: m/z 366 [M+H]$^+$, 266; $[\alpha]_D^{22}$ −46.2° (c=2.1 mg/ml in methanol).

EXAMPLE 17

In-Vitro Determination of Efficacy and Potency at the Human CB1 Receptor Expressed in CHO Cells Chinese Hamster Ovary (CHO) cells expressing the human CB1 receptor and a luciferase reporter gene were suspended in phenol red/serum free DMEM/F-12 nut mix containing penicillin/streptomycin (50 U/50 µg/ml) and fungizone (1 µg/ml) and seeded into 96 well plates at a density of 3×10$^4$ cells per well (100 µl final volume). Cells were incubated overnight (approx. 18 h at 37° C., 5% CO$_2$/95% air) prior to assay.

The test compound (10 mM solution in dimethylsulfoxide) was diluted in F12 Nut Mix to give a range of stock solutions from 0.11 mM to 0.11 nM. The stock solutions (10 µl) were added directly to the relevant wells. The plates were incubated at 37° C. for 5 h to allow agonist-induced expression of the luciferase enzyme. Under subdued light, LucLite substrate (Packard; reconstituted as per manufacturer's instructions; 100 µl) was added to each well. Plates were covered with Top Seal and then incubated at room temperature for 5 minutes before counting on the Packard TopCount (single photon counting, 0.01 minute count time, 5 minute count delay).

A "best-fit" curve was fitted by a minimum sum of squares method to the plot of counts per second (CPS) against compound concentration (M) to obtain an EC$_{50}$ value. Table 1 shows the pEC$_{50}$ values obtained for some representative compounds of the invention.

TABLE 1

| Example | Chemical name | Chemical structure | pEC$_{50}$ |
|---|---|---|---|
| 1 | (R)-3-Cyclohexyl-2,3-dihydro-6-(4-ethylpiperazin-1-ylcarbonyl)-pyrrolo[1,2,3-de]-1,4-benzoxazine hydrochloride salt | 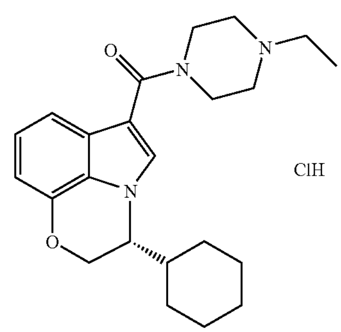 | 7.5 |
| 2 | (R)-3-Cyclohexyl-2,3-dihydro-6-[(S)-octahydro-2H-pyrido[1,2-a]pyrazin-2-ylcarbonyl]pyrrolo[1,2,3-de]-1,4-benzoxazine hydrochloride salt | 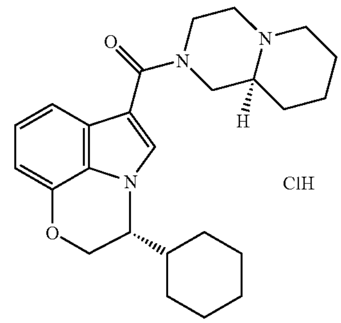 | 8.0 |

TABLE 1-continued

| Example | Chemical name | Chemical structure | pEC$_{50}$ |
|---|---|---|---|
| 4 | (R)-3-Cyclohexyl-2,3-dihydro-6-[(S)-3,4-dimethylpiperazin-1-ylcarbonyl]pyrrolo[1,2,3-de]-1,4-benzoxazine hydrochloride salt | 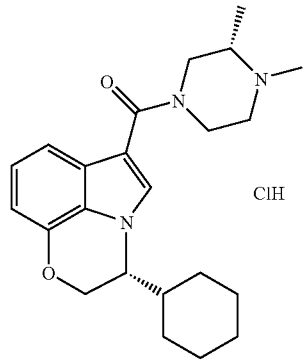 | 7.8 |
| 5C | (R)-3-Cyclohexyl-2,3-dihydro-6-[4-methylpiperazin-1-ylcarbonyl]pyrrolo[1,2,3-de]-1,4-benzoxazine hydrochloride salt | 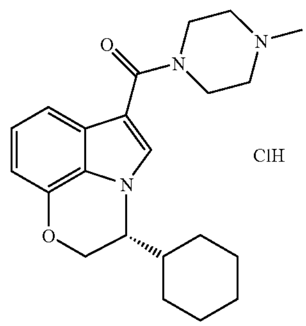 | 7.0 |
| 7 | (R)-3-Cyclohexyl-2,3-dihydro-6-[(cis)-3,4,5-trimethylpiperazin-1-ylcarbonyl]pyrrolo[1,2,3-de]-1,4-benzoxazine hydrochloride salt | 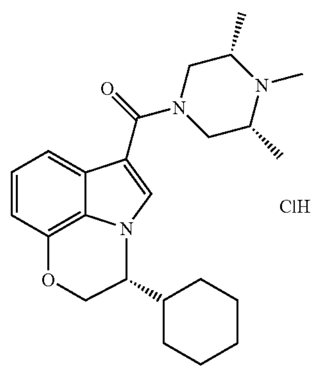 | 8.2 |
| 8 | (R)-3-Cyclohexyl-2,3-dihydro-6-[(cis)-3,5-dimethyl-4-ethylpiperazin-1-ylcarbonyl]pyrrolo[1,2,3-de]-1,4-benzoxazine hydrochloride salt | 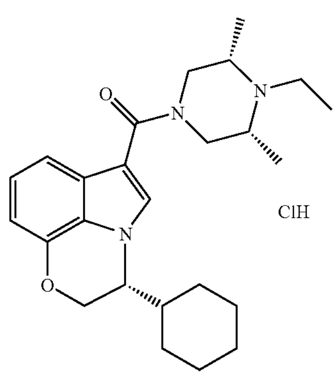 | 8.4 |

TABLE 1-continued

| Example | Chemical name | Chemical structure | pEC$_{50}$ |
|---|---|---|---|
| 9 | (R)-3-Cyclohexyl-2,3-dihydro-6-[(cis)-3,5-dimethyl-4-(2-hydroxyethyl)piperazin-1-ylcarbonyl]pyrrolo[1,2,3-de]-1,4-benzoxazine hydrochloride salt | 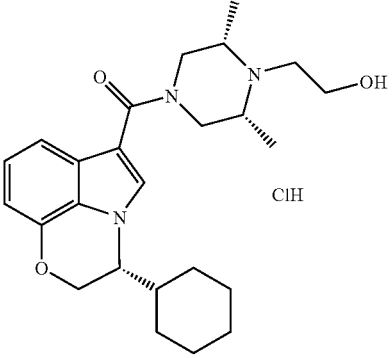 | 8.2 |
| 10 | (R)-3-Cyclohexyl-2,3-dihydro-6-[(cis)-3,5-dimethyl-4-(2-methoxyethyl)piperazin-1-ylcarbonyl]pyrrolo[1,2,3-de]-1,4-benzoxazine hydrochloride salt | 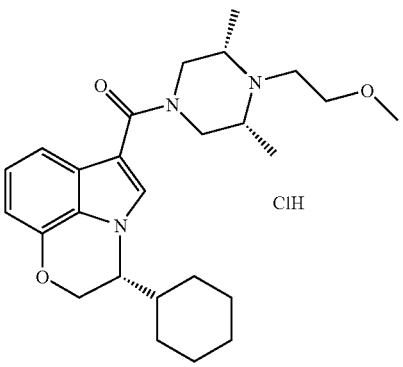 | 8.3 |
| 12B | (−)-4-Cyclopentyl-5,6-dihydro-1-(4-ethylpiperazin-1-ylcarbonyl)-4H-pyrrolo[3,2,1-ij]quinoline hydrochloride salt | 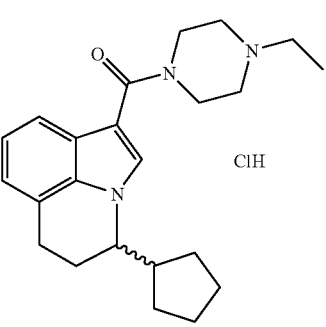 | 7.4 |
| 13 | (+)-4-Cyclohexyl-5,6-dihydro-1-(4-ethylpiperazin-1-ylcarbonyl)-4H-pyrrolo[3,2,1-ij]quinoline hydrochloride salt | 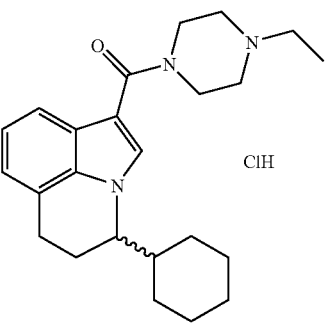 | 7.3 |

TABLE 1-continued

| Example | Chemical name | Chemical structure | pEC$_{50}$ |
|---|---|---|---|
| 14 | (+)-(4-Cyclohexyl-5,6-dihydro-1-(4-methylpiperazin-1-ylcarbonyl)-4H-pyrrolo[3,2,1-ij]quinoline hydrochloride salt | 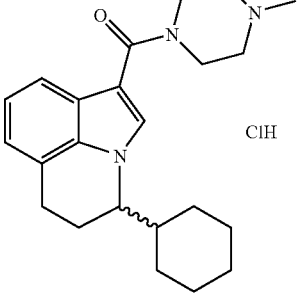 | 7.1 |
| 15 | (−)-(4-Cyclohexyl-5,6-dihydro-1-(4-ethylpiperazin-1-ylcarbonyl)-4H-pyrrolo[3,2,1-ij]quinoline hydrochloride salt | 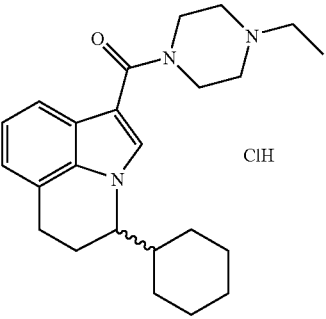 | 7.5 |
| 16 | (−)-(4-Cyclohexyl-5,6-dihydro-1-(4-methylpiperazin-1-ylcarbonyl)-4H-pyrrolo[3,2,1-ij]quinoline hydrochloride salt | 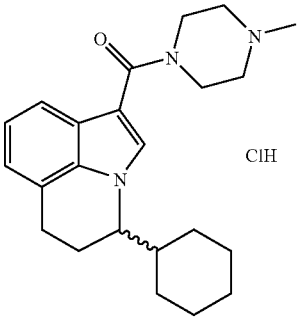 | 7.6 |

EXAMPLE 18

Tail Flick Latency in Mice

Mice were trained to sit still in a tail flick apparatus (Ugo Basile, Italy) whilst tail flick latency was measured. The tail was exposed to a focused beam of radiant heat at a point approximately 2.5 cm from the tip. Tail flick latency was defined as the interval between the appliance of the thermal stimulus and withdrawal of the tail. A 12 second cut-off was employed to prevent tissue damage. Four groups of eight mice were treated with vehicle or one of three doses of the test compound, administered intravenously (vehicle: saline 9 g/l; injection volume 10 ml/kg). Tail flick latency was measured before administration of the test compound and at regular intervals (typically 20, 40 and 60 minutes) after compound administration. The ED$_{50}$ was calculated at T$_{max}$.

The compounds of examples 2, 4, 14, 15 and 16 significantly increased the tail flick latency with an ED$_{50}$<5 μmol/kg.

The invention claimed is:
1. A tricyclic 1-[(indol-3-yl)carbonyl]piperazine derivative having the general Formula I

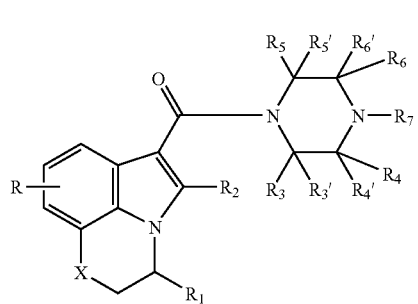

Formula I wherein
X is CH$_2$, O or S;

R represents 1-3 substituents independently selected from H, $(C_{1-4})$alkyl, $(C_{1-4})$alkyloxy and halogen;

$R_1$ is $(C_{5-8})$cycloalkyl;

$R_2$ is H or $(C_{1-4})$alkyl;

$R_3$, $R_3'$, $R_4$, $R_4'$, $R_5$, $R_5'$ and $R_6'$ are independently hydrogen or $(C_{1-4})$alkyl, optionally substituted with $(C_{1-4}$alkyloxy, OH or halogen;

$R_6$ is hydrogen or $(C_{1-4}$alkyl, optionally substituted with $(C_{1-4}$alkyloxy, OH or halogen; or $R_6$ forms together with $R_7$ a 4-7 membered saturated heterocyclic ring having only carbons as additional ring members; or $R_7$ is H, $(C_{1-4})$alkyl or $(C_{3-5})$cycloalkyl, the alkyl groups being optionally substituted with OH, halogen or $(C_{1-4})$alkyloxy; or a pharmaceutically acceptable salt thereof.

2. The tricyclic 1-[(indol-3-yl)carbonyl]piperazine derivative of claim 1, wherein R is H and $R_1$ is cyclopentyl or cyclohexyl.

3. The tricyclic 1-[(indol-3-yl)carbonyl]piperazine derivative of claim 1, wherein X is $CH_2$ or O.

4. The tricyclic 1-[(indol-3-yl)carbonyl]piperazine derivative of claim 1, wherein R, $R_2$, $R_3$, $R_3'$, $R_4'$, $R_5$, $R_5'$ and $R_6'$ are H; $R_4$, $R_6$ and $R_7$ are independently H or $(C_{1-4}$alkyl; or $R_6$ forms together with $R_7$ a 5- or 6-membered saturated heterocyclic ring having only carbons as additional ring members and $R_4$ is H or $(C_{1-4}$alkyl.

5. A pharmaceutical composition comprising a tricyclic 1-[(indol-3-yl)-carbonyl]piperazine derivative of claim 1 or a pharmaceutically acceptable salt thereof together with a pharmaceutically acceptable carrier therefor.

6. The tricyclic 1-[(indol-3-yl)carbonyl]piperazine derivative of claim 2, wherein X is $CH_2$ or O.

7. The tricyclic 1-[(indol-3-yl)carbonyl]piperazine derivative of claim 2, wherein R, $R_2$, $R_3$, $R_3'$, $R_4'$, $R_5$, $R_5'$ and $R_6'$ are H; $R_4$, $R_6$ and $R_7$ are independently H or $(C_{1-4}$alkyl; or $R_6$ forms together with $R_7$ a 5- or 6-membered saturated heterocyclic ring having only carbons as additional ring members and $R_4$ is H or $(C_{1-4}$alkyl.

8. The tricyclic 1-[(indol-3-yl)carbonyl]piperazine derivative of claim 3, wherein R, $R_2$, $R_3$, $R_3'$, $R_4'$, $R_5$, $R_5'$ and $R_6'$ are H; $R_4$, $R_6$ and $R_7$ are independently H or $(C_{1-4}$alkyl; or $R_6$ forms together with $R_7$ a 5- or 6-membered saturated heterocyclic ring having only carbons as additional ring members and $R_4$ is H or $(C_{1-4}$alkyl.

9. A method of treating pain in a patient in need of such treatment, comprising:

administering an effective amount of the compound according to claim 1 or a pharmaceutically acceptable salt thereof.

* * * * *